Figure 1:
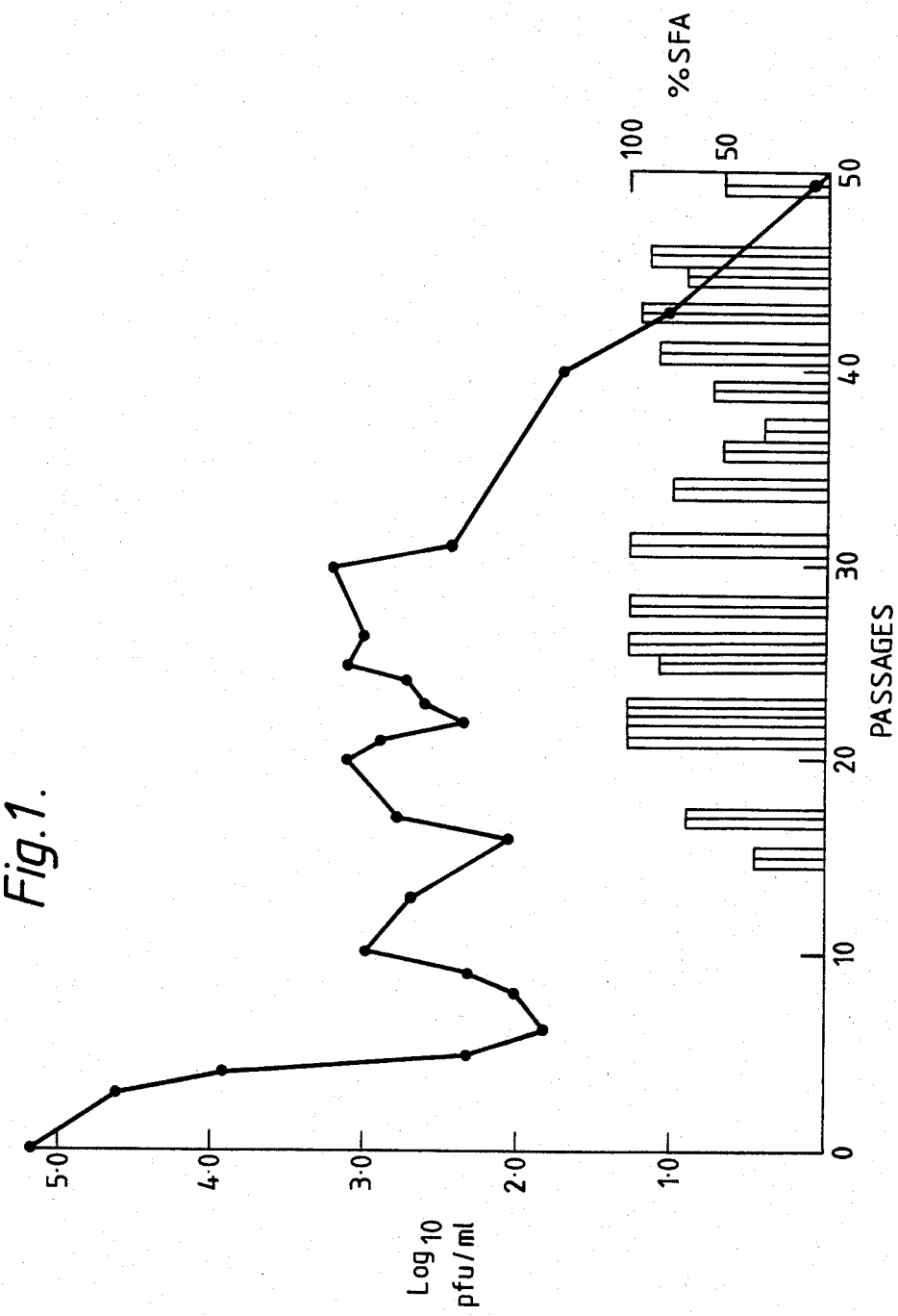

United States Patent [19]

Stott et al.

[11] Patent Number: 4,517,304

[45] Date of Patent: May 14, 1985

[54] PRODUCTION OF VIRAL ANTIGENS

[75] Inventors: Edward J. Stott; Lewis H. Thomas; Norma J. Jebbett, all of Newbury, England

[73] Assignee: National Research Development Corporation, London, England

[21] Appl. No.: 278,052

[22] Filed: Jun. 29, 1981

[30] Foreign Application Priority Data

Jul. 1, 1980 [GB] United Kingdom ............... 8021434

[51] Int. Cl.³ .................... G01N 33/54; C12N 5/00; C12Q 1/29; C12P 1/00
[52] U.S. Cl. .................................. 436/518; 424/89; 435/29; 435/41; 435/240; 436/811
[58] Field of Search ................ 424/1, 89; 435/240, 435/29, 41; 436/518, 811

[56] References Cited

U.S. PATENT DOCUMENTS 3,919,044 11/1975 Melnick et al. ............... 424/89
3,983,229 9/1976 Relyveld ....................... 424/89
4,112,068 9/1978 Cabasso ........................ 424/89
4,122,167 10/1978 Buynak et al. ................. 424/89

FOREIGN PATENT DOCUMENTS 1226743 3/1971 United Kingdom ............. 424/89
1560185 1/1980 United Kingdom ............. 424/89

OTHER PUBLICATIONS

Senterfit et al., Fed. Proc., 33, (3, part 1), 787 (1974).
Achong et al., J. Gen. Virol., 40; 175–181 (1978).
Smith et al., Inf. Immunity, 33:43–48 (1981).
J. Gen. Virol. (1974) 25, 1–10, Kaaden & Dietzschold.
The Journal of Infectious Diseases, vol. 136, No. 4, Oct. 1977, 519–530, Zaia & Oxman.
Nature, vol. 257, Oct. 23rd 1975, pp. 684–685, Powell.

*Primary Examiner*—Christine M. Nucker
*Attorney, Agent, or Firm*—Murray, Whisenhunt & Ferguson

[57] ABSTRACT

Antigens specific to respiratory syncytial virus are produced on the surface of cells by:
(1) culturing in vitro cells derived from a human or animal mucosa,
(2) inoculating the cultured cells with respiratory syncytial virus, and
(3) selecting virally infected cells from the culture.

The resulting cells or the viral antigen(s) when partially or completely isolated from the cells have immunological and diagnostic uses in respect of infection by respiratory syncytial virus and may be used to isolate viral antibodies. A specific cell strain NM7 produced by this method from bovine nasal mucosal cells has respiratory syncytial virus antigens on its surface and its corresponding, uninfected cell strain NM5 can be infected similarly.

17 Claims, 2 Drawing Figures

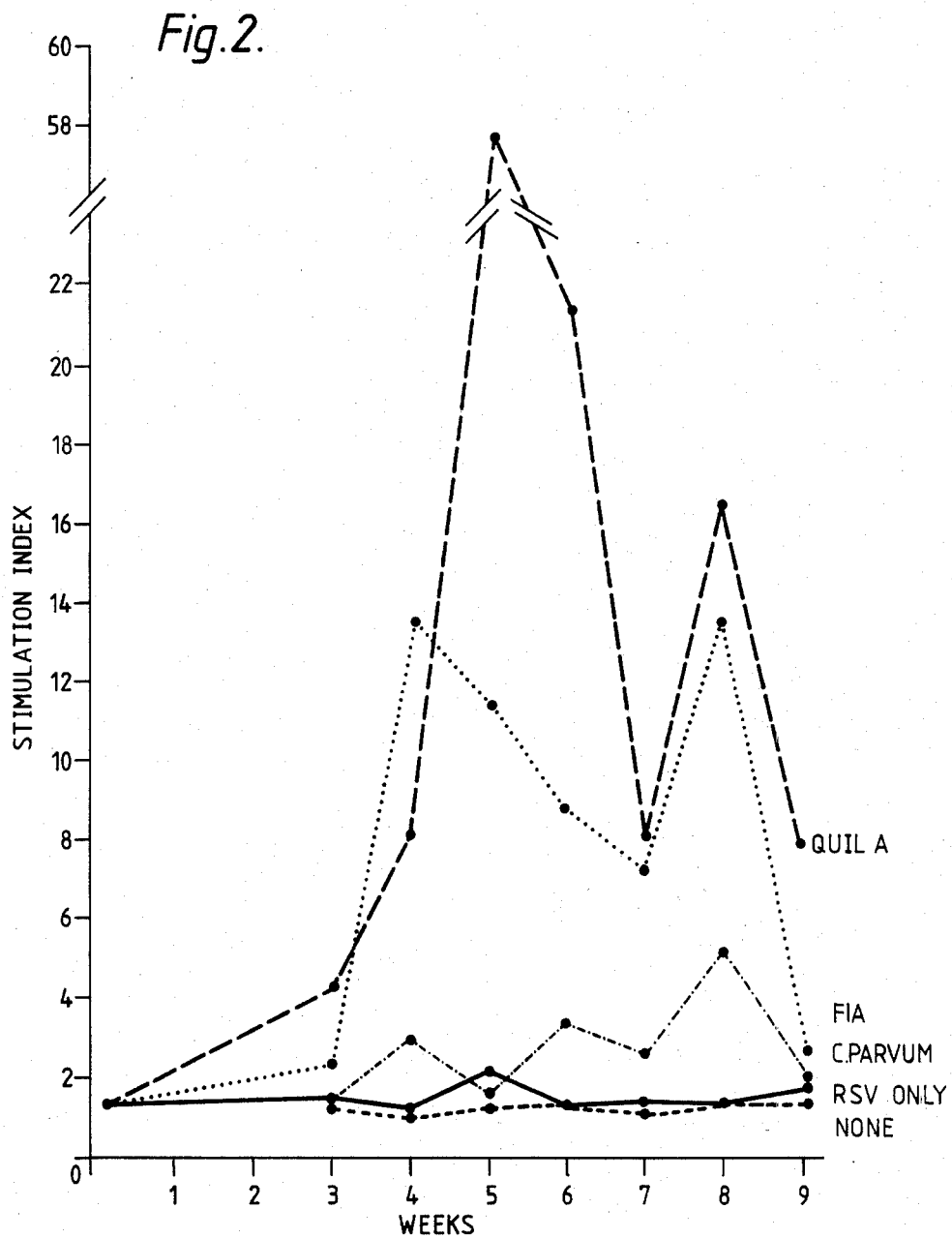

PRODUCTION OF VIRAL ANTIGENS

DESCRIPTION

The present invention relates to the production of respiratory syncytial virus (RSV)-specific antigens which are suitable for use in vaccines and also for diagnosis of infection by the virus (RSV). The present invention also relates to a particular cell strain useful in the production of RSV-specific antigens, and to a particular cell strain bearing these antigens on its cell surface.

In the past, viral diseases in animals have generally been controlled by vaccination with artificially attenuated strains of the virus or an antigenically-related virus. In the search for alternative vaccines suitable for administration to humans and animals, work has been carried out on virally infected cell cultures and it has been found that when some viruses replicate, they can induce the production of membrane or surface antigens on the cells which they infect. These antigens are specific to the particular virus and have been shown to react with immunoglobulins to that virus, the antisera prepared using them has been shown to neutralise the virus. There has thus been great interest in these virus specific antigens but, in many cases, these antigens are found on the membrane of relatively few of the cells infected.

It has now been found, in accordance with the present invention, that it is possible to prepare a cell population having antigens specific to respiratory syncytial virus on the surface of the cells. In this cell population, substantially all of the cells inoculated carry the antigens on their cell surface, at least at some time in their passage history.

Accordingly, the present invention provides a process of producing antigen(s) specific to respiratory syncytial virus, which process comprises:

(1) culturing in vitro cells derived from a human or animal mucosa, (2) inoculating the cultured cells with respiratory syncytial virus and allowing the virus to absorb, and (3) selecting virally infected cells from the culture.

The resulting cell strain obtained by this process has RSV-specific antigens associated with the cell surface, and both the cell strain so produced and the antigens which may be isolated from the cell surface form an aspect of the present invention. The antigens, whether isolated from the cells or not, may be provided in the form of a composition with a suitable carrier or diluent.

The cells used as starting material in the process of the present invention are derived from mucosae of humans or animals and preferably are derived from the respiratory tract. Particular sources of such cells are the trachea, lung and the nasal mucosa, and desirably they are cells from the nasal mucosa of cattle, especially bovine foetuses. Particular types of cells are those of cell strain SW129 NM5 described hereinafter which may serve as the cells to be inoculated in accordance with the invention.

It is possible, in accordance with the present invention, to inoculate the cultured cells, either before or after selection in stage (3), with a further virus, e.g. bovine virus diarrhoea virus (BVDV). Cells of cell strain SW129 NM7 described hereinafter may be superinfected to produce a multiple virus vaccine in this way. Thus, cells containing two or more types of viral antigen can be produced though it is important to ensure that none of the viruses interferes with the replication of the antigens of the other(s). In the case of inoculation with RSV alone, it has been shown that the resulting cell strain may be continually reseeded until it reaches a passage number where substantially 100% of the cells have antigens specific to RSV on their membrane.

The infected cells bearing the RSV-specific antigen may be used as an inoculum against diseases caused by the particular virus, as such after fixation or, alternatively, after further purification.

Fixation of the cells carrying the RSV-specific antigens on their surface may be carried out by treatment with a crosslinking agent, for example, glutaraldehyde. Glutaraldehyde is known to preserve or enhance the immunogenicity of antigenic structures while destroying infectivity and, in certain quantities, this is the effect it has on the RSV-infected mucosal cells of the present invention. Desirably, the concentration of glutaraldehyde used for fixation should not exceed 0.15% by weight, and more preferably should not exceed 0.075%. Periods for fixation will vary but will usually be from 1 to 5 minutes.

If, to avoid using fixed whole cells, it is desired to purify the viral antigen from the cell surface before incorporation into the vaccine, this may be done by washing the disrupted cells through immunoadsorbent columns bearing antisera to the antigens. The antigen(s) can thus be isolated completely from the cell surface or may be isolated partially but left attached to the membrane structure by removal of nuclei and cytoplasm from the cells. The latter procedure reduces the amount of nucleic acid associated with the antigen (nucleic acids being generally undesirable in a vaccine), but retains most of the antigenicity.

A further aspect of the present invention resides in a pharmaceutical composition suitable for use as a vaccine comprising an immunogenically effective amount, e.g. from $1\times10^5$ to $4\times10^6$ fixed cells per dose, of an antigen or antigens specific to respiratory syncytial virus, prepared in accordance with the present invention, in association with a pharmaceutically acceptable carrier or diluent. The antigen(s) may be present on the surface of a fixed cell or may be in partially or completely isolated form as discussed above. If desired, the composition may also contain antigens other than the RSV cell surface antigens of the present invention, either in association with the cells or as separate entities, thus providing a multiple vaccine. Examples of such antigens are BVDV, parainfluenza virus type 3(Pi-3), *Mycoplasma dispar* and *Mycoplasma bovis* antigens.

Compositions may be in any suitable solid or liquid form and presented in conventional manner for parenteral or oral administration. Thus, the composition may, for example, be in the form of an injectable solution or in the form of a tablet, capsule, solution, suspension or emulsion. Suitable carriers or diluents for use in these compositions are Freund's incomplete adjuvant (FIA), *Corynebacterium parvum* (*C.parvum*) and Quil-A, preferably the latter which is partially purified saponin and produces less reaction at the site of injection. Humans or animals may be vaccinated against diseases caused by respiratory syncytial virus, and optionally other viral diseases, by administering to the humans or animals a composition as defined above.

An alternative use for the cells bearing viral antigens, or the completely or partially isolated viral antigens, produced in accordance with the present invention, is in the diagnosis of diseases caused by RSV by detection of RSV antibody in a biological sample, e.g. serum, taken from a human or animal. Any known method of immunological diagonsis may be used for this purpose. Thus, qualitative precipitation techniques may be used, but preferably quantitative techniques are used, for example immunoadsorption whereby the antigens are rendered insoluble by cross-linking with, for example, glutaraldehyde, contacted with a serum sample so that any antibody present binds to the antigens, releasing the antibody and determining the amount, and possibly also distribution between the classes, of immunoglobulin. Alternatively, a radioimmunoassay (RIA) involving inhibition of binding of radioactively labelled antiserum by the samples containing unknown quantities of the antibodies can be used. Preferably, however, immunofluoroescence techniques are used where a fluorescent marker such as fluorescein or rhodamine is coupled to the viral antigens and binding of antibody to the marked antigen is detected.

An antigen or cell strain of the present invention may also be coupled to a solid phase and used in affinity purification to isolate RSV antibody from a biological sample by contacting said sample with the solid phase and subsequently separating RSV antibody from the solid phase.

The present invention also provides a method for the propagation of a cell strain bearing viral antigens produced in accordance with the present invention, which comprises culturing the cells in vitro in a nutrient culture medium therefor.

Such a medium might be an isotonic medium containing essential salts, amino acids and vitamins buffered to physiological pH and supplemented with growth-promoting substances, such as animal sera. An example is the organ culture medium identified later in Table 1. The cell strains produced by the process of the present invention may thus be grown up and passaged to maximise the production of the virus-specific antigens. Alternatively, they may be preserved in liquid nitrogen from which they can be recovered as desired to provide a readily available source of said antigens; dimethyl sulphoxide is desirably used as a cryoprotectant.

The method of culturing the cells can be by organ culture, tissue culture or cell culture but is desirably carried out by organ culture when proliferating cells from around the piece of organ will provide the virus-specific antigens. Any known method may be used which can, for example, increase the yield of the cells and hence of the virus specific antigens. Thus the growth medium can be adapted for this purpose, e.g. by the incorporation of insulin in a concentration of, for example, 5 µg/ml, or the cells may be adapted to roller, sepharose bead or suspension culture. As a further alternative, the cells could be fused, for example to lymphoma, myeloma or fibroblast cells to enable them to multiply more rapidly and thus to increase the rate at which the viral antigens are formed. The latter technique may be particularly useful where the mucosal cell membrane to which the viral antigens are attached could cause anti-host reactions in a human or animal to be inoculated. To reduce these reactions, the membranes can be derived from cells of the same species as that to be inoculated. Alternatively, a cell strain derived from an animal may be fused with human fibroblast, myeloma or lymphoma cells to produce a fused cell suitable for use in a human vaccine. Desirably, as previously indicated, such a fused cell will have its nuclei and cytoplasm removed to reduce the level of nucleic acid, often considered undesirable in a human vaccine.

A particular cell strain (designated SW129 NM5) which also forms an aspect of the present invention, has been produced and shown to be capable, when inoculated with RSV, of producing virus-specific antigens on its cell surface in accordance with the present invention. NM5 appears capable of containing and replicating the antigens of another virus simultaneously and thus represents a cell strain having the potential to produce a multi-virus vaccine. An example of another virus which may be inoculated into SW129 NM5 is BVDV. A cell strain corresponding to cell strain SW129 NM5 but actually infected with RSV during culturing has been designated SW129 NM7 and forms a still further embodiment of the present invention. It has been shown, at least at some passage numbers, to have antigen specific to RSV on 100% of the cell population.

The two cell strains SW129 NM5 and SW129 NM7 have been prepared by the following method:

The nasal mucosa was removed from a bovine foetus (SW 129), cut into squares approximately 5 mm × 5 mm and placed on previously scratched areas of plastic petri dishes. Organ culture medium (see Table 1 below for composition) was then added until the base of the ciliated epithelium was covered. The dishes were then incubated at 35° C. for three days.

TABLE 1

| Organ Culture Medium (400 ml) | |
| --- | --- |
| Eagles basal medium (Flow Laboratories) × 10 in double distilled water | 320 ml |
| Foetal calf serum (heat inactivated at 56° C. for 30 mins) | 20 ml |
| Sodium bicarbonate (5.6%) | 10 ml |
| Bovine plasma albumen (9%) | 4 ml |
| Tryptose phosphate broth (Difco) | 20 ml |
| HEPES buffer pH 7.2 (1M) | 10 ml |
| Penicillin (10,000 units/ml) | 4 ml |
| Streptomycin (10,000 µg/ml) | 4 ml |
| Kanamycin (20,000 µg/ml) | 4 ml |
| Mycostatin (2,500 µg/ml) | 4 ml |

The cultures were examined by reflected light and only those with vigorous ciliary activity were used. One thousand plaque-forming uits (pfu) of respiratory syncytial virus (RSV) were dropped onto eight cultures and another eight cultures acted as uninoculated controls. After allowing the virus to absorb for 2 hrs at 35° C., the cultures were washed three times in medium and further incubated at 35° C. The medium was changed twice each week and samples were collected for titration of virus infectivity.

By 14 days after infection, cells had proliferated extensively on the plastic around the nasal mucosa tissue of both infected and control cultures. After removal of the piece of organ culture, the proliferating cells were removed from the plastic by incubation at 37° C. with trypsin-versene solution. (The trypsin-versene solution contained EDTA (0.02% in phosphate buffered saline) and Difco 1:250 Trypsin (0.25% in phosphate buffered saline) in a ratio of 4:1 by volume.) The cells were resuspended in growth medium and seeded into 4 oz medical flat bottles. Each week thereafter the cells from one bottle were reseeded into two. The cell strain derived from uninfected cultures was named SW129 NM5 and that from RSV infected cultures SW129 NM7 and these strains and the virus specific antigens on the cell surface of SW129 NM7 represent further embodiments of the present invention.

The cell strain SW129 NM7 is a cell strain containing respiratory syncytial virus and also antigen specific to that virus on its membrane cell surface and is a product produced in accordance with the process of this invention. The corresponding cell strain SW129 NM5 uninfected with RSV is also of significance in the present invention when the cell strain SW129 NM7 is to be used to diagnose infection by RSV. Thus, it can act as a control in that, in all respects other than the possession of the virus and the viral antigens, it is identical with the cell strain SW129 NM7. Alternatively, it can itself be used as a cell culture for inoculation with RSV or another virus and growing up of the virus with concomitant production of the viral antigens.

The invention is further described with reference to the accompanying drawings, in which:

FIG. 1 is a graph showing the amount of virus shed into a medium ($\log_{10}$ pfu/ml) and percentage of SW129 NM7 cells carrying antigen on their surface (% SFA) at various passage levels; and FIG. 2 shows variations in the stimulation index in calves as a function of the number weeks following vaccination with GFC formulations.

The cell strains SW129 NM5 and SW129 NM7 have been deposited with the Collection Nationale de Cultures de Microorganismes (C.N.C.M.) at the Institut Pasteur, Paris on June 25, 1980 and have been given the accession numbers I-124 and I-125 respectively. They can be characterised as follows:

Both SW129 NM5 and SW129 NM7 cells appear fibroblastic and spindle-shaped when attached to glass and are up to 100 μm long. Rounded cells in suspension have a diameter of 10 μm. Between 1% and 5% of SW129 NM7 cells are multinucleate giant cells. Electron microscopy of ultrathin sections of SW129 NM5 cells reveals a highly vacuolated cytoplasm containing electron-dense debris and a small number of microvilli on the cell surface. In NM7 cells vacuolation is increased, microvilli have proliferated and appear to polarise in one area. Many SW129 NM7 cells also contain dense intracytoplasmic inclusions.

The range of antigens in the SW129 NM7 cells has been determined by immune precipitation of $^{35}$S methionine-labelled RS virus-infected calf kidney cells using sera obtained from calves vaccinated with glutaraldehyde-fixed SW129 NM7 cells. Strong precipitation of all the known virus-specific polypeptides was observed and, in addition, a previously unrecognised protein of 17,000 daltons was detected (see Table 2 below). This indicates that glutaraldehyde-fixed SW129 NM7 cells contain the full complement of RSV antigens in a fully immunogenic form. The antigens are capable of raising antibodies of types IgG$_1$, IgG$_2$ and IgM as is indicated in Example 4 hereinafter.

TABLE 2

| | | Immune precipitation by | |
|---|---|---|---|
| Virus polypeptide | Molecular weight | Standard antiserum (G141) | Vaccine antisera |
| 1. Large glycoprotein | 77,600 | + | + |
| 2. protein | 49,800 | + | + |
| 3. Major glycoprotein | 45,900 | +++ | +++ |
| 4. Nucleoprotein | 41,400 | +++ | +++ |
| 5. protein | 34,600 | ++ | ++ |
| 6. Matrix protein | 26,800 | +++ | +++ |
| 7. Small glycoprotein | 20,700 | + | ++ |
| 8. protein | 18,900 | + | ++ |
| 9. protein | 17,100 | − | + |
| 10. protein | 13,200 | + | ++ |

− <50 cpm
+ 100–500 cpm
++ 501–1000 cpm
+++ >1000 cpm

Chromosome preparations from both SW129 NM5 and SW129 NM7 at passages 22 and 27 reveal predominantly acrocentric autosomes, a long submetacentric X chromosome and metacentric Y chromosome characteristic of the bovine male. The chromosomes of 58 SW129 NM5 nuclei and 65 SW129 NM7 nuclei were counted and over 60% of cells and counts between 55 and 64, close to the bovine diploid number of 60. There was no evidence of polyploidy nor of a predominant heteroploid number which might imply malignant transformation of the cells and render the cells unsuitable for use as a vaccine.

The passage history of the cell strains SW129 NM5 and SW129 NM7 was examined. Both SW129 NM5 and SW129 NM7 cells were passaged from 1 to 2 bottles every week and formed confluent monolayers in 5 to 7 days, up to about passage 35. Thereafter cell division slowed, and ceased by passage 50.

Between passages 5 and 50 all SW129 NM7 cells contained RSV antigen in their cytoplasm as shown by staining acetone-fixed cells with fluorescent antibody. The amount of virus shed into the medium ($\log_{10}$ pfu/ml) and percentage of SW129 NM7 cells carrying antigen on their surface (%SFA) at various passage levels is shown in FIG. 1 of the accompanying drawings. The titre of released virus declined from $10^{4.7}$ pfu/ml at passage 3 to $10^{1.8}$ at passage 6 and thereafter fluctuated between $10^2$ and $10^3$ until about passage 30 when the titre gradually fell until virus eventually became undetectable by passage 50. The proportion of cells bearing RSV antigen on their surface rose to 100% at passage 21 and remained so until about passage 30 after which some fluctuation occurred.

The SW129 NM5 and SW129 NM7 cells have been recovered from liquid nitrogen storage on nine occasions. They have had essentially the same passage history each time.

SW129 NM5 and SW129 NM7 cells between passages 20 and 30 have been stained by fluorescent antibody specific for bovine syncytial virus or bovine virus diarrhoea virus eight times and shown to be consistently negative. Cells from both lines have been inoculated twice into calf kidney cells and calf testis monolayers in the presence of RSV antibody. No cytopathogenic agents were detected despite passaging of the cell cultures for six weeks. No mycoplasmas were isolated from cells at passage 25.

As further characterisation of the cell strains, the ability of SW129 NM5 and SW129 NM7 cells to support the replication of five bovine viruses was examined by inoculating monolayered cultures, between passages 16 and 30, with parainfluenzavirus type 3 (Pi-3), bovine virus diarrhoea virus (BVDV), the SD-1 strain of bovine rhinovirus type 1 (RV-1) the EC-11 strain of bovine rhinovirus type 2 (RV-2) and respiratory syncytial virus. Virus was allowed to absorb to the cells for 2 hours at 37° C., the cultures were then washed three times and sampled immediately after washing and 3, 7, 10 and 14 days later. The results are shown in Table 3 below. Pi-3 and BVDV produced high yields in SW129 NM5 and SW129 NM7 cells. The two rhinoviruses produced higher titres in SW129 NM7 than in SW129 NM5 cells, although this effect was most marked with RV-2 which failed to replicate at all in SW129 NM5. The RSV multiplied in SW129 NM5 but not in SW129 NM7 cells. Such autologous interference is a characteristic of persistently infected cell lines.

TABLE 3

| Virus | Harvest | Titre* in indicated cells | |
|---|---|---|---|
| | | NM5 | NM7 |
| Pi-3 | Wash | 4.3 | 4.3 |
| | Yield+ | 7.7 | 8.2 |
| BVDV | Wash | 2.8 | 2.6 |
| | Yield | 6.4 | 6.3 |
| RV-1 | Wash | 1.7 | 1.7 |
| | Yield | 3.9 | 4.8 |
| RV-2 | Wash | 2.0 | 2.3 |
| | Yield | 0.9 | 4.9 |
| RSV | Wash | 2.0 | 2.1 |
| | Yield | 5.7 | 2.2 |
| None | Wash | 0 | $1.7^x$ |
| | Yield | 0 | $2.4^x$ |

*Mean of 2 experiments for RSV and no virus, mean of 3 experiments for other viruses. (expressed as log 10 pfu/ml)
+Maximum obtained during 14 days of incubation
$^x$Persistent RSV in NM7 cells.

In preparing the SW129 NM7 cells in a form suitable for incorporation into a vaccine, cells ($10^6$/ml) were treated for various times at 4° C. with 0.075% glutaraldehyde. After 1 minute infectivity was destroyed but the proportion of cells stained by fluorescent antibody was unchanged after 15 minutes, although the intensity of fluorescence decreased after 5 minutes. This data indicated that cells fixed for 5 minutes were anitgenic but not infectious, and were therefore suitable to be incorporated into a vaccine. Alternatively, the antigen may be partially or completely isolated from the SW129 NM7 cells before being incorporated in such a vaccine.

SW129 NM7 cells or their partially or completely isolated viral antigens are also useful in the diagnosis and isolation techniques described hereinbefore. When carrying out diagnostic tests using SW129 NM7 cells, it is desirable to repeat the tests using SW129 NM5 cells as a control.

The present invention will now be illustrated by the following Examples.

EXAMPLE 1

Twelve calves were vaccinated subcutaneously with $4 \times 10^6$ glutaraldehyde-fixed SW129 NM7 cells (GFC) emulsified in Markol-Arlacel A oil adjuvant. Three weeks after two doses had been given three weeks apart, the calves were challenged intranasally with $10^6$ pfu of live RSV. All calves responded serologically to the vaccine by a single radial haemolysis test and eleven by a neutralization test (see Table 4 below). After challenge, only one vaccinated calf was infected and shed virus on only one day compared with 9 unvaccinated calves which were all infected and shed virus for 5 to 11 days.

TABLE 4

| Calf t = | Serological responses* | | | | | Virus shedding | |
|---|---|---|---|---|---|---|---|
| | Neutralising titre | | | Haemolysis zone | | | |
| | 0 | 6 weeks | 9 weeks | 0 | 6 weeks | 9 weeks | Peak titre log pfu/ml | Duration (days) |
| Control Group | | | | | | | | |
| M434 | <2 | <u><2</u> | 8 | 0 | 0 | 23 | 3.4 | 11 |
| M618 | <2 | <u><2</u> | 4 | 0 | 0 | 25 | 3.1 | 9 |
| M619 | <2 | <u><2</u> | 4 | 0 | 0 | 41 | 3.2 | 7 |
| M448 | <2 | <u><2</u> | 4 | 0 | 0 | 23 | 2.8 | 5 |
| M449 | <2 | 2 | 16 | 0 | 0 | 11 | 2.0 | 7 |
| M655 | 2 | <u><2</u> | 16 | 0 | 0 | 27 | 3.1 | 5 |
| M474 | <2 | <u><2</u> | 8 | 0 | 0 | 43 | 3.9 | 7 |
| M687 | <2 | 4 | 32 | 0 | 0 | 48 | 4.1 | 5 |
| M689 | 2 | 2 | 8 | 0 | 0 | 49 | 1.5 | 5 |
| Vaccine Group | | | | | | | | |
| M440 | <u><2</u> | 8 | 8 | 0 | 114 | 92 | 0 | 0 |
| M634 | <u><2</u> | 32 | 32 | 0 | 92 | 118 | 0 | 0 |
| M639 | <u>2</u> | 16 | 32 | 0 | 106 | 106 | 0 | 0 |
| M206 | <u><2</u> | 8 | 16 | 0 | 114 | 114 | 0 | 0 |
| M646 | <u><2</u> | 128 | 128 | 0 | 110 | 110 | 0 | 0 |
| M651 | <u>2</u> | 32 | 16 | 0 | 99 | 46 | 0 | 0 |
| M662 | <u>2</u> | 64 | 64 | 0 | 110 | 110 | 0 | 0 |
| M663 | <u>2</u> | 64 | 64 | 0 | 110 | 66 | 0 | 0 |
| M664 | <u><2</u> | 64 | 32 | 0 | 99 | 46 | 0 | 0 |
| M693 | <u><2</u> | 64 | 64 | 0 | 106 | 72 | 0 | 0 |
| M694 | <u>2</u> | 16 | 16 | 0 | 95 | 78 | 0 | 0 |
| M697 | 4 | <u>2</u> | 16 | 13 | | 126 | 122 | 2.4 |

Calves in the group were vaccinated at time t = 0 and t = 3 weeks and all calves were challenged at time t = 6 weeks.
*Figures underlined indicate a significant response to vaccine or to challenge.

EXAMPLE 2

Groups of six calves were given glutaraldehyde-fixed SW129 NM7 cells with Freund's incomplete adjuvant in doses varying from $2 \times 10^6$ to $1 \times 10^5$ cells. Two doses were given subcutaneously and calves were bled six weeks after the second dose. Anitbody responses were measure by single radial haemolysis (SRH), neutralization and radioimmunoassay (RIA) and the results are given in Table 5 below, which show that there was no significant difference in the antibody produced over the range of antigen dilutions used.

TABLE 5

| Dose (no of cells) | no. of calves | SRH mean zone area (mm$^2$) Pre | SRH mean zone area (mm$^2$) Post | Neutralization mean titres Pre | Neutralization mean titres Post | RIA mean titres (log$_{10}$) Pre | RIA mean titres (log$_{10}$) Post |
|---|---|---|---|---|---|---|---|
| 2 × 10$^6$ | 6 | 0 | 109 ± 21 | 1.6 | 16 | 0.2 | 5.0 |
| 1 × 10$^6$ | 6 | 0 | 99 ± 23 | 2.1 | 6.3 | 0.3 | 4.2 |
| 5 × 10$^5$ | 6 | 0 | 117 ± 21 | 2.8 | 8 | 0.8 | 4.1 |
| 2 × 10$^5$ | 6 | 0 | 89 ± 30 | 3.5 | 6.3 | 0.3 | 3.0 |
| 1 × 10$^5$ | 6 | 0 | 116 ± 20 | 1.8 | 10 | 0 | 4.4 |
| None | 9 | 0 | 0 | 2.6 | 1.9 | 0 | 0 |

EXAMPLE 3

Multiple Vaccine

Glutaraldehyde-fixed SW129 NM7 cells (GFC) at 2×10$^6$ per dose were combined with parainfluenzavirus type 3, *Mycoplasma dispar* and *Mycoplasma bovis* antigens to produce a multiple vaccine and compared with a vaccine of SW129 NM7 cells alone. Both vaccines contained Freund's incomplete adjuvant, and were injected subcutaneously three times at intervals of three weeks. RS virus antibodies induced by the vaccines were measured by single radial haemolysis and the results are given in Table 6 below.

TABLE 6

| Vaccine | No. of calves | SRH antibody mean zone area mm$^2$ pre | SRH antibody mean zone area mm$^2$ post | Challenge No. of calves | Challenge virus Isolated |
|---|---|---|---|---|---|
| GFC | 9 | 0 | 116.3* | 3 | 0 |
| Multiple | 10 | 0 | 97.1* | 3 | 1 |
| *M. bovis* | 9 | 0 | 0 | 3 | 3 |

*Difference not statistically significant p > 0.5 by Students' t-test.

Although the mean zone area of 10 calves given the multiple vaccine was 19.2 mm$^2$ less than that of 9 calves given SW129 NM7 cells alone, the difference was not statistically significant. Three calves in each group and three calves given *M.bovis* vaccine alone were challenged with live virus, three months after the final dose of vaccine. RS virus was recovered from the 3 calves given *M. bovis* vaccine, one of 3 given multiple vaccine and none of 3 given RS vaccine.

EXAMPLE 4

The glutaraldehyde-fixed cells (GFC) were combined (2×10$^6$ cells per dose) with three different adjuvants: Freund's incomplete adjuvant (FIA); *Corynebacterium parvum* (*C. parvum*) and Quil-A. Of the calves, six received GFC with FIA, three received GFC with *C. parvum* (5 mg/dose), three received GFC with Quil-A (1 mg/dose) and three received GFC with no adjuvant. Nine calves acted as unvaccinated controls. Two doses of each vaccine were given subcutaneously 3 weeks apart.

Antibody responses to the vaccines were assessed by neutralization tests and single radial haemolysis (SRH) tests on sera collected before the first and three weeks after the second vaccination and the results are given in Tables 7 and 8 respectively.

TABLE 7

| Vaccine | No. | No of responses | Mean titre Pre | Mean titre Post |
|---|---|---|---|---|
| FIA + GFC | 6 | 5 | 1.6 | 16 |
| C. parv. + GFC | 3 | 0 | 3.2 | 2.5 |
| Quil-A + GFC | 3 | 2 | 2.0 | 13 |
| GFC only | 3 | 0 | 1.8 | 1.8 |
| None | 9 | 0 | 2.5 | 2.0 |

TABLE 8

| Vaccine | No. | No of responses | Mean titre Pre | Mean titre Post |
|---|---|---|---|---|
| FIA + GFC | 6 | 6 | 0 | 109 ± 21 |
| C. parv. + GFC | 3 | 2 | 0 | 60 ± 53 |
| Quil-A + GFC | 3 | 3 | 0 | 127 ± 15 |
| GFC only | 3 | 0 | 0 | 0 |
| None | 9 | 0 | 0 | 0 |

These results show that there were no responses in unvaccinated animals nor in calves given GFC without adjuvant. Significant SRH responses were seen in 2 of 3 calves given GFC with *C. parvum*. However, the responses of calves given GFC with FIA or Quil-A were greater than those of calves given GFC with *C. parvum*, by both serological tests.

The class of antibody to RSV produced in each of the tests was determined by radioimmunoassay (RIA) and the results are given in Table 9 below.

TABLE 9

| Vaccine | Pre IgG$_1$ | Pre IgG$_2$ | Pre IgA | Pre IgM | Post IgG$_1$ | Post IgG$_2$ | Post IgA | Post IgM |
|---|---|---|---|---|---|---|---|---|
| FIA + GFC | 0.2 | 0 | 0 | 0 | 5.0 | 3.2 | 0.2 | 1.8 |
| C. parv. + GFC | 1.3 | 0 | 0 | 0 | 3.0 | 1.3 | 0 | 1.1 |
| Quil-A + GFC | 0 | 0 | 0 | 0 | 6.1 | 1.6 | 0 | 1.2 |
| GFC only | 0 | 0 | 0 | 0 | 1.0 | 0 | 0 | 0.5 |
| None | 0 | 0 | 0 | 0 | 0 | 0 | 0 | 0 |

Antibody was not detected in unvaccinated calves and only low levels of IgG$_1$ and IgM in calves given GFC without adjuvant. In calves given GFC with *C. parvum*, mean titres of IgG$_1$, IgG$_2$ and IgM were 10$^3$, 10$^{1.3}$ and 10$^{1.1}$ respectively. In calves given GFC with either FIA or Quil-A, IgG$_1$ titres were 100- and 1000-fold higher respectively, but although IgG$_2$ titres were almost 100-fold higher in calves given FIA they were only 2-fold higher in those given Quil-A when compared with calves given *C.parvum*.

The antigenic specificity of vaccine-induced antibody was determined by mixing sera collected three weeks after the second vaccination with standard radiolabelled RSV-induced antigens, precipitating the antigen-antibody complexes with *Staph. aureus* and analysing the precipitated viral antigens by polyacrylamide gel electrophoresis. The results are given in Table 10 below.

TABLE 10

| Virus polypeptide | Molecular weight | cpm precipitated (mean of sera from 3 calves) No adjuvant | cpm precipitated (mean of sera from 3 calves) C. parvum | cpm precipitated (mean of sera from 3 calves) Quil-A | cpm precipitated (mean of sera from 3 calves) FIA |
|---|---|---|---|---|---|
| 1. Large glycoprotein | 77,600 | <50 | <50 | 120 | 67 |
| 2. protein | 49,800 | <50 | <50 | 87 | 56 |
| 3. Major glycoprotein | 45,900 | <50 | 81 | 3570 | 1760 |
| 4. Nucleoprotein | 41,400 | <50 | 133 | 1540 | 1030 |
| 5. protein | 34,600 | <50 | <50 | 590 | 150 |

TABLE 10-continued

| Virus polypeptide | Molecular weight | cpm precipitated (mean of sera from 3 calves) | | | |
|---|---|---|---|---|---|
| | | No adjuvant | C. parvum | Quil-A | FIA |
| 6. Matrix protein | 26,800 | <50 | 80 | 1540 | 1310 |
| 7. Small glycoprotein | 20,700 | <50 | 52 | 1040 | 520 |
| 8. protein | 18,900 | <50 | <50 | 1090 | 600 |
| 9. protein | 17,100 | <50 | <50 | 220 | <50 |
| 10. protein | 13,200 | <50 | <50 | 760 | 360 |

It can be seen from these results that virus-specific polypeptides were not precipitated by sera from calves given GFC without adjuvant. Sera from calves given GFC with *C. parvum* precipitated the major glycoprotein, nucleoprotein and the putative matrix protein. Sera from calves given GFC with FIA or Quil-A precipitated large amounts of all nine virus-induced polypeptides but calves vaccinated with Quil-A precipitated significantly more of the 35,000 molecular weight protein and the previously unrecognised protein of 17,000 daltons.

The results of these experiments show that Quil-A appears to be at least as effective as Freund's incomplete adjuvant for GFC and, in addition, has the advantage of inducing less reaction at the site of injection.

RSV-specific cell-mediated immunity, as determined by in vitro lymphocyte transformation (LT) activity, was examined in the calves vaccinated for this experiment. The lymphocyte population involved in the LT responses was determined using lymphocytes separated after direct anti-immunoglobulin red cell rosette formation, on a ficoll-Isopaque gradient. LT activity to RSV was associated only with T lymphocytes. There did not appear to be a direct correlation between the magnitude of the LT response and levels of serum antibodies as detected by virus neutralization or the single radial haemolysis test.

The unvaccinated calves and those given GFC without adjuvant showed no significant LT. Low levels of stimulation were seen with lymphocytes from calves given GFC with *C. parvum*. In contrast, high levels of LT activity were seen in calves given GFC with either FIA or Quil-A. Two weeks after a second vaccination, the mean stimulation index was 5-fold higher in calves given GFC with Quil-A than in those given GFC with FIA. These results are shown in FIG. 2 of the accompanying drawings.

We claim:

1. A process of producing a cell strain useful in the production of antigen(s) specific to respiratory syncytial virus, which process comprises:
   (1) culturing in vitro cells derived from a human or animal respiratory tract mucosa,
   (2) inoculating the cultured cells with respiratory syncytial virus, and
   (3) selecting virally infected cells from the culture.
2. A cell strain according to claim 1 having its surface antigens fixed by treatment with a cross linking agent.
3. A cell strain according to claim 2 having its surface antigens fixed by treatment with glutaraldehyde.
4. Respiratory syncytial virus antigen(s) when partially or completely isolated from the surface of the cells of a cell strain as claimed in claim 1.
5. A composition comprising cells of a cell strain as claimed in claim 1 and a carrier or diluent.
6. A composition comprising viral antigen(s) as claimed in claim 4, and a carrier or diluent.
7. A pharmaceutical composition comprising an immunogenically effective amount of antigen(s) as claimed in claim 4, and a pharmaceutically acceptable carrier or diluent.
8. A pharmaceutical composition comprising an immunogenically effective amount of antigen(s) attached to cells of a cell strain as claimed in claim 1, and a pharmaceutically acceptable carrier or diluent.
9. A method of diagnosing respiratory syncytial virus infection by detecting antibody to that virus in a biological sample taken from a human or animal, which method comprises utilizing cells of a cell strain as claimed in claim 1 in an immunological diagnostic method.
10. A method of diagnosing respiratory syncytial virus infection by detecting antibody to that virus in a biological sample taken from a human or animal, which method comprises utilizing antigen(s) as claimed in claim 4, in an immunological diagnostic method.
11. A method according to claim 9 in which the diagnostic method involves immunoadsorption, a radioimmunoassay or immunofluorescence and is carried out on a serum sample taken from a human or animal.
12. A method according to claim 10 in which the diagnostic method involves immunoadsorption, a radioimmunoassay or immunofluorescence and is carried out on a serum sample taken from a human or animal.
13. A method of isolating a respiratory syncytial virus antibody from a biological sample which comprises contacting the biological sample with, in the solid phase, cells of a cell strain as claimed in claim 1, and subsequently separating viral antibody from the solid phase.
14. A method of isolating a respiratory syncytial virus antibody from a biological sample which comprises contacting the biological sample with, in the solid phase, antigen(s) as claimed in claim 4, and subsequently separating viral antibody from the solid phase.
15. A method of propagating a cell strain as claimed in claim 1, which method comprises culturing the cells in a nutrient culture medium therefor.
16. A method of immunising against respiratory syncytial virus infections in a host which comprises administering to that host an immunogenically effective amount of antigen(s) as claimed in claim 4.
17. A method of immunising against respiratory syncytial virus infections in a host which comprises administering to that host an immunogenically effective amount of antigen(s) attached to cells of a cell strain as claimed in claim 1.

* * * * *

UNITED STATES PATENT AND TRADEMARK OFFICE
CERTIFICATE OF CORRECTION

PATENT NO. : 4,517,304

DATED : May 14, 1985

INVENTOR(S) : STOTT et al

It is certified that error appears in the above-identified patent and that said Letters Patent is hereby corrected as shown below:

Column 11 lines 51 through 58: cancel claim 1 and replace by --1. Cell strain SW129 NM7 (CNCM No.I-125) comprising cells carrying respiratory syncytial virus antigens on their surface.--

Column 12 line 16 insert --or 2-- after "1"
Column 12 line 22 insert --or 2-- after "1"
Column 12 line 40 insert --or 2-- after "1"
Column 12 line 59 insert --or 2-- after "1"

Signed and Sealed this

Eighth Day of April 1986

[SEAL]

Attest:

DONALD J. QUIGG

Attesting Officer

Commissioner of Patents and Trademarks